United States Patent [19]

Bordenca

[11] 4,174,406
[45] Nov. 13, 1979

[54] TERPENYLAMINOALKANOL FISH TOXICANTS

[75] Inventor: Carl Bordenca, Rocky River, Ohio

[73] Assignee: SCM Corporation, New York, N.Y.

[21] Appl. No.: 800,376

[22] Filed: May 25, 1977

Related U.S. Application Data

[63] Continuation of Ser. No. 599,244, Jul. 24, 1975, abandoned, which is a continuation-in-part of Ser. No. 468,907, May 10, 1974, abandoned.

[51] Int. Cl.$^2$ .......................... A01N 9/20; A01N 9/24
[52] U.S. Cl. .................................................. 424/325
[58] Field of Search .......................... 424/325; 260/584

[56] References Cited

U.S. PATENT DOCUMENTS

| | | | |
|---|---|---|---|
| 2,383,564 | 8/1945 | Ralston et al. | 424/325 |
| 2,541,089 | 2/1951 | Nikavitz | 260/584 |
| 2,689,263 | 9/1954 | Schmidle et al. | 260/584 |
| 2,964,530 | 12/1960 | Zenitz | 424/325 |
| 3,483,254 | 12/1969 | Shen et al. | 424/325 |
| 3,659,015 | 4/1972 | Hoffmann | 424/325 |

FOREIGN PATENT DOCUMENTS 1165930  3/1964  Fed. Rep. of Germany.

*Primary Examiner*—Douglas W. Robinson
*Attorney, Agent, or Firm*—A. Joseph Gibbons

[57] ABSTRACT

Certain terpenylaminoalkanol compounds have been found to be selective piscicides useful in controlling fish species populations including carp and white sucker.

16 Claims, No Drawings

TERPENYLAMINOALKANOL FISH TOXICANTS

This application is a Rule 60 Continuation Application based on copending application Ser. No. 599,244 filed July 24, 1975, which in turn was a continuation-in-part of application Ser. No. 468,907 filed May 10, 1974, both of which have been abandoned in favor of the present application. Benefit of earlier filing under 35 USC 120 is claimed herein.

This invention relates to new piscicides. Although several general fish toxicants are known as shown in U.S. Pat. No. 3,076,743 there is a great need for agents which will selectively control undesirable species of fish without harmful effect on desirable species present in the same body of water. The common carp is known to be destructive of the habitat of desirable game fish and consequently there is a particular need for controlling carp populations. Presently there are two important registered fish toxicants which are widely used to kill carp and other species of fish—Rotenone and antimyein. These toxicants suffer from the disadvantages that they are non-selective for carp and their activity is adversely affected by waters of high pH.

An object of the present invention is to provide a selective fish toxicant for controlling fish populations comprising a carrier and an effective amount of about 20–95 percent by weight of certai terpenylaminoalkanol compounds and derivatives thereof.

Another object of this invention is to provide a process for treating ponds and other bodies of water whereby undesirable fish populations can be controlled or eliminated without substantial injury to other desirable fish, including game and edible fish, by treating such water with an effective amount in the range of 0.03 to 10 parts, preferably 0.03 to 1.5 parts, per million parts of water of certain terpenylamenoalkanol toxicant or water soluble salt thereof.

A further object is to provide a piscicide that is compatible with nature and will readily deactivate, detoxify and be substantially innocuous to other organisms indigent to such bodies of water.

Yet, another object is to provide a piscicide and process for the control of common carp and white sucker.

The term "piscicide" refers to a toxicant or chemical that when applied to the water habitat of fish tends to poison and otherwise control by reducing the population of certain fish, especially undesirable fish, while being innocuous toward other desirable fish species.

The term carp as used in this invention refers to the common carp (*Cyprinus carpio*) as distinguished from goldfish (*Carassius auratus*) and grass carp (*Ctenopharyngodon idella*) species.

The terms "selective control" or "selectively controlling" refer to the use of toxicant to irradicate or lower the population of one or more species of fish in a particular water habitat where other more desirable species coexist.

The particular toxicants of the present invention are useful in such control due to the fact that different species of fish are not equally affected or harmed by the same dosage of toxicant and thus have different LD50 values (concentration producing 50 percent mortality). This difference in LD50 values allows one to predict the concentration necessary to selectively control a fish species. These differences are shown in Table 1 of the examples which follow. Although the particular dosage of toxicant to be applied will be subject to experimental conditions, it will usually fall within the range of 0.005 to 10 parts of toxicant per million parts of water treated.

The term "desirable species" and "undesirable species" may very widely with the location and purpose of the water body. The common carp (*Cyprinus carpio*) and white sucker (*Catostomus commersoni*) are commonly deemed undesirable species, especially in the northern United States and Canada. Game fish and edible fish such as coho salmon, chinook salmon, rainbow trout, brown trout, lake trout, bass, bluegill and walleye are classified as desirable species for purposes of this invention. Similarly classified as desirable species are goldfish, fathead, minnows, banded killifish, and yellow perch. Species such as catfish may be desirable or nondesirable depending on the geographical location, presence of other more desirable fish species and whether or not they are needed for food purposes.

The terpenylaminoalkanol toxicants of this invention can be represented by the formula:

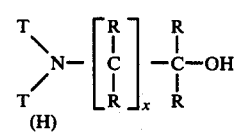

Formula I wherein:

T is a radical selected from the group consisting of acyclic monoterpenyl, isobornyl and tetrahydrogeranyl;

R is independently hydrogen or a lower alkyl radical containing 1 to 4 carbon; and x is an integer of from 1 to 4.

The acyclic monoterpenyl radicals falling within the scope of the above formula include citronellyl, bupleuryl, geranyl, neryl, lavandulyl, linalyl, and myrcenyl. Advantageous and preferred selective toxicant compounds are those wherein T represents geranyl, neryl and linalyl. Especially preferred toxicants are the di terpenylaminoalkanols for example, N-(2-hydroxyethyl) digeranylamine and N-(3-hydroxypropyl) digeranylamine.

Further groups representative of T in Formula I above include partially and fully hydrogenated acyclic monoterpenyl groups and the isobornyl group. Preferred within this sub-group are the mono and di (3,7-dimethyloctyl) toxicants derived from geranyl and/or linalyl aminoalkanols. Especially preferred are the compounds N-(2-hydroxyethyl) di-(3,7dimethyloctyl) amine and N-(2-hydroxyethyl) diisobornylamine.

Compounds falling within the scope of the above formula have limited water solubility but can be made soluble by converting them into corresponding ammonium salts (or tertiary amine salts) by reacting them with an appropriate acid. Acids useful for preparing the acid-addition salts include inorganic acids, such as hydrohalic acids (e.g., hydrochloric and hydrobromic), sulfuric acid, nitric acid, and phosphoric acid and organic acids such as, for example, oxalic, maleic, tartaric, citric, acetic and succinic acid. Such acid salts are readily soluble in water and can be formulated in water for application to the ponds and/or other aquatic area fish habitats. It is contemplated that both the hydroxyalkylamine and their water-soluble salts will be useful in the practice of this invention.

Preferred salts are hydrohalide salts, for example the hydrochloride and hydrobromide salts. These salts are conveniently formed from readily available hydrogen chloride and hydrogen bromide gases or from aqueous acid solution. When the anhydrous salt is desired it may be prepared by adding a stochiometric amount of an anhydrous ether solution of the hydrogen halide to an ether solution of the appropriate terpenylaminoalkanol. The amine hydrohalide (or acid salt) usually forms as a white solid which can be filtered and further purified by recrystalization. Commercially it will usually be more feasible to react the terpenylaminoalkanol with the stoichimetric amount of the desired aqueous acid to form an aqueous solution of the salt which may be conveniently diluted further with water to the desired concentration for storage and shipment. It is preferred to prepare salt solutions of the order of 20-75 percent by weight active toxicant since these appear more stable over prolonged periods of storage. Especially preferred are solutions of about 50 weight percent toxicant.

It is also within the scope of the invention to use quaternary salts of the desired terpenylaminoalkanol in place of the acid salts described above. Thus a wide variety of salts having water solubility greater than the free aminoalkanol are provided. The preparation of quaternary salts is well-known. They are synthesized in a procedure similar to the anhydrous acids salts with the exception that a reactive $C_{1-12}$ hydrocarbyl halide is used in place of the hydrogen halide. Simple quaternary salts may be made from methyl and ethyl bromide. Preferred quaternary salts are those prepared by the reaction of terpenylaminoalkanol with allyl bromide or chloride, geranyl bromide or chloride, benzyl halides and naphthyl halides. The quaternary salt prepared from myrcenyl chloride is especially preferred because of its availability and the desirable properties of the resulting salts.

The free aminoalkanols and their salts may be further formulated with conventional carriers and dispersing agents to meet the various conditions of climate, water temperature, alkalinity, acidity and hardness of the treated water. In general where the water is acidic it is desirable to use the free amine or the quaternary salt when the water is basic all three forms of the terpenylaminoalkanol toxicant or mixtures thereof may be used. In general the best formulation will be determined by the characteristics of the water to be treated. When the free terpenylaminoalkanol is used it can be dissolved or dispersed in typical liquid carriers; commercially available alcohols are satisfactory. Dispersions in inert hydrocarbon diluents can be used where conditions permit. Common wetting agents and surfactants may be used to obtain uniform compositions of the order of 20-95% active toxicant. When the toxicant chosen is tha acid or quaternary salt of the aminoalkanol, it is usually preferred for economical reasons to dissolve or disperse these in water.

Typical solid carriers on which the terpenylaminoalkanols may be deposited include finely divided inorganic solid materials, siliceous minerals, clays, bentonite, attapulgite, fullers earth, diatomacous earth, kaolin, mica and talc as well as other prepared siliceous materials including silica gels, aerogels and fume silicas. When solid carriers are used basic claysaare generally preferred, especially when the pH of the pond water is on the acid side. The compositions help to prevent rapid deterioration of the active terpenylaminoalkanol.

Application doses of the active aminoalkanols of this invention and their inorganic acid salts suitably are from 0.03 to 10 parts per million parts of water treated. Of course, these quantities will vary somewhat depending on the particular characteristics of the water. Specific factors including the presence of particular microorganisms will effect the optimum quantity of toxicant to be used. Treatment lower than about 0.03 parts per million will generally be insufficient to control the trash fish while concentrations of toxicant above 3.0 parts per million usually will be toxic both to the desirable species as well as to the trash fish and should be avoided when selectivety is desired. It is preferred to treat the ponds and other bodies of water to be protected with incremental amount of the toxicant over a period of 1-3 days gradually building up the concentration of active terpenylaminoalkanol to the optimum value. The present toxicants usually are effective in about 10-100 hours after treatment of the water is made. The particular hydrocarbyl aminoalkanols of this invention are ecologically desirable; laboratory studies show these aminoalkanols deactivate within about seven days.

It is preferred to name the toxicants of this invention as amines rather than alcohols. However, it would not be incorrect to use nomenclature where the alcohol portion is treated as the principal function. In this manner the above compounds would be also correctly identified as di-(3,7-dimethyloctyl) aminoethanol and 2-(diisobronyl) aminoethanol, respectively.

Advantageous alkanol groups in Formula I are primary, secondary, and tertiary alkanol groups containing between 2 and 8 carbon atoms and include those radicals derived by removing a hydrogen atom from an unhydroxylated carbon atom from ethanol, n-propanol, 2-methyl-2-propanol, 2-methyl-1-propanol, n-butanol, isobutanol, tertiary butyl alcohol, and the various normal isomeric pentanols, hexanols, heptanols and octanols. Although tertiary alcohols and secondary alcohols are useful fish toxicants, piscicides having the primary alcohol structures are preferred. Especially preferred are ethanols and substituted ethanols wherein the terpenylamino function is separated from the hydroxy group by two carbon atoms.

Specific compounds which are tertiary amines and which are useful in the practice of this invention include the following compounds and their citronellyl, and linalyl counterparts:
N-(3-hydroxypropyl) digeranylamine
N-(1-methyl-2-hydroxyethyl) digeranylamine
N-(1,1-dimethyl-2-hydroxyethyl) digeranylamine
N-(1-ethyl-2-hydroxyethyl) digeranylamine
N-(2-hydroxyethyl) digeranylamine
N-(5-hydroxypentyl) digeranylamine
N-(3-hydroxybutyl) digeranylamine
N-(1-ethyl-2-hydroxyethyl) di(3,7-dimethyloctyl) amine
N-(5-hydroxypentyl) digeranylamino
N-(3-hydroxypropyl) digeranylamine
N-(2-hydroxyethyl) di(3,7-dimethyloctyl) amine
N-(2-hydroxyethyl) diisobornylamine Specific compounds which are secondary amines and which are useful in the practice of this invention include the following:
N-(3-hydroxypropyl) geranylamine
N-(2-hydroxypropyl) linalylamine
N-(1,1-dimethyl-2-hydroxyethyl) citronellylamine
N-(1-ethyl-2-hydroxyethyl) lavandulylamine
N-(3-hydroxybutyl) bupleurylamine
N-(5-hydroxypentyl) nerylamine
N-(2-hydroxyethyl) 3,7-dimethyloctylamine N-(1-methyl-2-hydroxyethyl) isobornylamine

SYNTHESIS

The compounds of this invention may be prepared by modification of methods well-known in the literature. Common general methods for the preparation of substituted aminoalkanols are shown in U.S. Pat. No. 2,363,081 as intermediates for the preparation of various local anesthetic esters and in the Journal of the American Chemical Society publications by Ringk et al (65 p. 1222, 1943), Cope et al (66 pp. 1733-1747, 1944), Pierce et al (71 1765, 1949). Other synthetic approaches occasionally used include preparation of the corresponding amino ketone followed by reduction of the keto group to yield the desired alcohol and hydrogenation of the corresponding oxazolidines.

A preferred synthetic method for the preparation of the compounds of this invention comprises heating the corresponding hydrocarbyl halide with the hydroxy lower alkylamines such as, for example 2-hydroxy-1,1-dimethylethylamine and 3-hydroxy-propylamine at a temperature in the range from 40° C. to 160° C. in the presence of an acid acceptor. If desired, an excess of the lower hydroxyalkyl amine can be used as the acid acceptor. The reaction is preferably carried out in an organic solvent inert under the conditions of the conditions of the reaction. For example methanol, ethanol, propanol and higher alcohol and ethers may be used but hydrocarbons such as benzene, xylene and the like are generaly preferred. The acid acceptor generally is a basic substance which forms water-soluble by-products salts with the evolved hydrogen halide and includes both inorganic metal hydroxides and tertiary amines such as tri-ethylamine and pyridine. When a hydrocarbon solvent is used, the by-product amine hydrochloride will be an insoluble solid which can be easily separated from the reaction product by filtration. Work-up is conveniently carried out by filtering the amine hydrochloride, washing the organic phase with water, evaporating the solvent and distilling the product. In some cases where the products are solids, recryalization is preferred to distillation.

The following examples, representative of the invention, are not intended to limit the scope of the invention in any manner. All percentages are weight percentages and all temperatures are in degrees centigrade unless otherwise specified.

EXAMPLE 1

N(2-hydroxy-1,1-dimethylethyl) Geranylamine

Commercial myrcene hydrochloride, 290 grams (1.12 moles containing about 67% by weight usable geranyl and neryl chlorides) was slowly added with stirring over a four hour period to 220 grams (2.25 moles) of molten 2-amino-2-methyl-1-propanol maintained at 55°-64° C., and the stirring was continued at this temperature for an additional 2½ hours after completion of the addition. The reaction mixture was made alkaline with 20% aqueous sodium hydroxide and further heated under reflux for one hour. After cooling, the organic oil was separated, washed with water, and dried with anhydrous magnesium sulfate. The oil was distilled under vacuum through a short Vigreaux column and the fraction boiling over the range 100°-125° C. at 0.07 mm Hg absolute was collected and identified as 99% pure N-(2-hydroxy-1,1-dimethylethyl) geranylamine (41% yield). NMR spectroscopy identified the product as a mixture containing both the geranyl and neryl isomers.

EXAMPLE 2

N-(2-hydroxy-1,1-dimethylethyl) Digeranylamine

The vacuum distillation described in Example 1 was continued after removing the monogeranylamine. After discarding an intermediate fraction N-(2-hydroxy-1,1-dimethylethyl) digeranylamine was isolated in 21% yield, b.p. 170-190 at 0.07 mm Hg absolute. MNR spectroscopy showed this fraction to be 98% pure (mixture of geranyl and neryl isomers).

EXAMPLE 3

N-(2-hydroxy-1,1-dimethylethyl) Tetrahydrogeranylamine

A solution of 20 grams of N-(2-hydroxy-1,1-dimethylethyl)geranylamine in 25 milliliters of glacial acetic acid was treated with 0.4 grams of platinum oxide ("Adams Catalyst") and subjected to hydrogenation at 60 psi hydrogen pressure, for three hours. The resultant solution was filtered to remove the catalyst, diluted with aqueous sodium hydroxide and the crude product was allowed to solidify. When recrystallized from acetone a white solid was obtained meeting 59°-61° C. Alternatively, purification could be effected by distillation under reduced pressure (b.p. 108°-155° C. at 0.17 mm Hg absolute). The structure of the product was verified by NMR spectroscopy.

EXAMPLE 4

N-(2-hydroxyethyl) gernaylamine was prepared in a manner similar to the procedure of Example 1 except that the alcohol used was 2-aminoethanol.

EXAMPLE 5

N-(2-hydroxyethyl) digeranylamine was prepared in a manner similar to the procedure described in Examples 1 and 2. Distillation under vacuum was continued after isolating the compound described in Example 4 and to give the product which was a liquid, b.p. 170°-175° C. at 0.2 mm. hg absolute; $M_D(25)$ 1.496; sp. gr. 0.870/20° C.

EXAMPLE 6

N-(2-hydroxypropyl) geranylamine was prepared in a manner similar to the procedure of Examples 1 and 2 except that amino alcohol used was 2-hydroxypropylamine. N-(2-hydroxypropyl) digeranylamine was obtained as a higher boiling fraction.

EXAMPLE 7

N-(1-hydroxymethyl-propyl) di (3,7-dimethyloctyl)amine was prepared in a manner similar to the procedure of Example 3 except that the starting material used was N-(1-hydroxymethyl-propyl) digeranylamine.

EXAMPLE 8

N-(2-hydroxyethyl) digeranylamine was tested as a selective fish toxicant in outdoor pools stocked with various fish species and lined with black plastic using 50% water soluble formulations (hydrochloride salt). The formulation was added to each of four pools of 4,000-liter capacity at concentrations of 0.10, 0.15, 0.20, and 0.30 mg/liter. Another pool containing the same number, size, and species of fish served as a control. The test water had algal blooms, a pH of about 8.5, and a total hardness of about 200 mg/liter as CaCo₃. The temperature was cool enough (15°-16°C.) to permit the use of trout.

Fish were obtained from state and federal hatcheries and maintained prior to testing by a trained fish culturist. Fish of total length 2-5 cm were used in laboratory tests while for outdoor tests small fish (4-6 cm in length) and larger carp and buffalo (*Ictiobus cyprinellus*) were used.

In all tests 10 fish of each were exposed to selective concentrations of the toxicant. Mortalities were observed and recorded at 1,2 and 6 hours on the first day and once daily thereafter, during 96 hour exposure.

Laboratory tests were also conducted in soft water 12° C. wherein the toxicant was evaluated against fifteen species of fish including both cold and warm water varieties. In Table 1, the LC 50 toxicity values for N-(2-hydroxyethyl) digeranylamine is shown for various species. LC50 is defined as the amount (mg/liter) of toxicant required to kill 50 percent of the particular fish species at 95% confidence interval. Thus, the 96 hour LC50 against carp (*Cyprinus carpio*) is 0.050 mg/liter as compared to 0.37 for smallmouth bass and 0.72 for bluegill. Chinook, coho salmon, rainbow trout, goldfish, fathead, minnow, banded killfish, and walleye were more resistant to the toxicant than carp (*Caprinus carpio*) or white suckers (*Castostmus commersoni*).

EXAMPLE 9

The effect of the various toxicants on common invertebrate species was determined in a static test conducted 17° C. The invertebrates tested were collected from natural populations or purchased from commercial suppliers. They were held in soft water in fiberglass tanks in the laboratory or in outdoor plastic swimming pools. Mortality was observed during holding, and only healthy organisms were used for the toxicity tests. At least 10 organisms of nine species were exposed to each concentration in static tests.

Tubifex was by far the most sensitive species and the LC50 (0.054) is significantly different from LC50's for the toxicant for other species (Table 2). Tubificids were as sensitive to the material as the most sensitive fish. Water fleas (*Daphnia magna*), seed shrimp (*ostracod*), and snails (*physa sp.*) were approximately as sensitive to the toxicant as fish other than carp and white sucker. Dragonfly naiads (*Macromia sp.*), backswimmers (*Notonecta sp.*) snails (*Fleurocera sp.*), and clams (*Corbicula sp.*) and *Sphaerium sp.*) were more resistant than most of the fishes, and the LC50 values for these invertebrates are approximately 10 times those for fish.

EXAMPLE 10

Outdoor pool tests were conducted using 50% formulation of the toxicant N-(2-hydroxyethyl) digeranylamine as indicated in Example 8. As shown in Table 3, small common carp (4-6 cm) and rainbow trout were completely eliminated at all concentrations above 0.10 mg/l in 96 hour exposures. If selective control of white sucker and common carp is desired in an environment which includes rainbow trout, one should employ an effective concentration of toxicant which is at least as great as 0.05 mg/liter but less than 0.1 mg/liter. As a practical fishery practice in the northern United States and Canada, rainbow trout are not usually stocked in bodies of water containing the common carp species; the habitat conditions including water temperature and available oxygen of these species are usually quite different. Common carp and rainbow trout have quite different oxygen and temperature requirements and these differences generally preclude both species cohabitating under natural conditions. In this case the useful range to control common carp and white sucker can be much broader, i.e. 0.1 to 0.3 mg/liter. Some white suckers and larger carp (19 cm) survived exposures of 0.10 and 0.15 mg/liter, but none survived concentrations of 0.2 mg/liter or higher. Species having complete survival at 0.3 mg/liter include goldfish, grass carp (*Ctenopharyngodon idella*), black bullhead (*Ictaiurys melas*), green sunfish, bluegill, largemouth bass (*Micropterus salmoides*), and walleye. Some fathead, minnows, channel catfish, and yellow perch died at 0.30 mg/liter of toxicant, but all survived lower concentrations.

EXAMPLE 11

Evaluation of di(terpenyl) amino alkanol compounds where the terpenyl groups are linalyl, citronellyl, and the alkanol groups are 2-hydroxyethyl 1,1-dimethyl-2-hydroxyethyl, 1-methyl-2-hydroxyethyl, 2-hydroxypropyl, 3-hydroxypropyl, 4-hydrobutyl, and 5-hydroxypentyl in tests equivalent to those indicated in Examples 8 and 10 will produce substantially the same selective control of carp species.

EXAMPLE 12

To determine the influence of pH of the water used on the toxicity of the terpenylaminoalkanols evaluated, experiments were conducted with green sunfish (*Lepomis cyanellus*) using soft water at 12° C. and chemically buffered over the range of pH 6 to pH 9. The results shown in Table 4 indicate that the selective toxicants are not deactivated by alkaline water, but rather increase significantly in activity. Thus, 1.85 mg/liter is needed for LC50 control at pH 6.0, but only 0.26 mg/liter is needed for the equivalent control at pH 9.0. These results show that it is difficult to state in advance the optimum level of toxicant needed to selectively control a fish species and that the hardness of water the pH and the temperature all must be carefully considered in arriving at the optimum level of toxicant to be applied to a particular body of water.

EXAMPLE 13

The selective toxicant, N-(2-hydroxyethyl)-digeranylamine was evaluated against bluegill in waters of hardness of 12, 44, 170, and 300 p.p.m., total hardness as CaCo₃. The 96-hour LC 50's (mg/liters) for bluegill corresponding to the above hardness were 0.84, 0.72, 0.46, and 0.33 respectively. Generally the harder waters are also higher in pH. antimycin The above results demonstrate the unexpected improvements of the instant terpenylaminoalkanol toxicants over the only two registered fish toxicants, Rotenone and antimycin. Both Rotenone and antimmycin are non-selective for carp and are adversely affected by pH. In contrast the specific aminoalkanols of this invention are selective to carp (*Caprinus carpio*) and effective in waters of high pH.

TABLE 1

Toxicity of N-(2-hydroxyethyl) Digeranylamine (tech) to fish at 12 C

| Species | LC50 and 95% confidence interval (mg/liter) at | | | |
|---|---|---|---|---|
| | 3 hours | 6 hours | 24 hours | 96 hours |
| Coho salmon | 0.320 | 0.240 | 0.200 | 0.142 |
| (*Oncorhynchus kisutch*) | 0.281–0.364 | 0.217–0.265 | 0.185–0.216 | 0.119–0.170 |
| Chinook salmon | 0.300 | 0.210 | 0.167 | 0.129 |
| (*Oncorhynchus tschawytscha*) | 0.268–0.335 | 0.178–0.248 | 0.149–0.187 | 0.111–0.150 |
| Rainbow trout | 0.220 | 0.189 | 0.187 | 0.136 |
| (*Salmo gairdneri*) | 0.190–0.260 | 0.158–0.226 | 0.150–0.230 | 0.100–0.160 |
| Brown trout | 0.0955 | 0.0742 | 0.0700 | 0.0647 |
| (*Salmo trutta*) | 0.0826–0.110 | 0.0641–0.0852 | 0.0597–0.0820 | 0.536–0.0780 |
| Lake trout | 0.109 | 0.0700 | 0.0470 | 0.0570 |
| (*Salvelinus* | 0.0876–0.136 | 0.0561–0.0882 | 0.0364.0.580 | |
| | | | 0.0380–0.0680 | |
| *namaycush*) | | | | |
| Goldfish | — | — | 0.961 | 0.290 |
| (*Carassius auratus*) | | | 0.845–1.09 | 0.259–0.321 |
| Carp | — | 1.34 | 0.0718 | 0.0507 |
| (*Cyprinus carpio*) | | 0.780–2.30 | 0.0631–0.0816 | 0.0447–0.0588 |
| Fathead minnow | — | 1.55 | 0.560 | 0.303 |
| (*Pimephales promelas*) | | 1.06–2.27 | 0.424–0.740 | 0.283–0.325 |
| White sucker | 0.540 | 0.136 | 0.0690 | — |
| (*Catostomus commersoni*) | 0.392–0.743 | 0.112–0.164 | 0.0543–0.0876 | |
| Banded killifish | 7.20 | 2.77 | 1.32 | 0.792 |
| (*Fundulus diaphanus*) | 4.11–12.6 | 2.33–3.29 | 1.00–1.74 | 0.699–0.898 |
| Green sunfish | — | — | 0.640 | 0.640 |
| (*Lepomis cyanellus*) | | | 0.462–0.884 | 0.462–0.884 |
| Bluegill | 1.56 | 1.13 | 0.720 | 0.720 |
| (*Lepomis macrochirus*) | 1.30–1.87 | 0.958–1.33 | 0.651–0.796 | 0.651–0.796 |
| Smallmouth bass | 1.36 | 0.480 | 0.420 | 0.237 |
| (*Micropterus dolomieui*) | 0.970–1.91 | 0.377–0.611 | 0.349–0.515 | 0.187–0.300 |
| Largermouth bass | 1.40 | 0.530 | 0.380 | 0.360 |
| (*Micropterus salmoides*) | 1.05–1.86 | 0.494–0.575 | 0.354–0.408 | 0.319–0.406 |
| Walleye | 2.78 | 1.03 | 0.346 | 0.239 |
| (*Stizostedion vitreum*) | 1.62–4.76 | 0.796–1.33 | 0.273–0.438 | 0.187–0.306 |

TABLE 2

Toxicity of N-(2-hydroxyethyl) Digeranylamine (tech) to invertebrates in static bioassays at 17 C

| Species | LC50 and 95% confidence interval (mg/liter) at | | | | |
|---|---|---|---|---|---|
| | 1 hour | 3 hour | 6 hours | 28 hours | 96 hours |
| Aquatic olgochaete[1] | 4.30 | 2.64 | 2.35 | 0.280 | 0.054 |
| (*Tubifex tubifex*) | 3.20–5.77 | 1.72–4.05 | 1.85–2.98 | 0.140–0.559 | 0.033–0.087 |
| Water flea[1] | 8.00 | 3.95 | 3.00 | 0.800 | 0.160 |
| (*Daphnia magna*) | 7.02–9.12 | 3.27–4.77 | 2.41–3.73 | 0.704–0.908 | 0.101–0.252 |
| Seed shrimp or | — | — | 3.00 | 1.00 | 0.320 |
| ostracod[1] | | | 1.95–4.62 | 0.560–1.79 | 0.145–0.707 |
| Dragonfly naiad[2] | — | — | — | — | 2.00 |
| Macromia sp.) | | | | | 1.02–3.91 |
| Backswimmer[2] | 9.15 | 8.35 | 8.30 | 4.90 | 3.45 |
| Notonecta) sp.) | 8.57–9.77 | 7.28–9.60 | 5.64–7.04 | 3.98–6.03 | 2.80–4.25 |
| Snail[1] | — | — | — | 10.3 | 2.68 |
| Pleurecera sp.) | | | | 0.56–16.0 | 1.68–4.26 |
| Snail[1] | 6.30 | 2.25 | 0.945 | 0.580 | 0.460 |
| Physa sp.) | 5.48–7.25 | 1.64–3.09 | 0.766–1.17 | 0.501–0.671 | 0.389–0.543 |
| Asiade clam[1] | — | — | — | 56.0 | 9.60 |
| Corbicula sp.) | | | | 49.2–63.7 | 5.91–15.6 |
| Fingernail clam[1] | — | — | — | — | 11.5 |
| Sphaerium sp.) | | | | | 7.68–17.2 |

[1] Limed spring water of 22–36 mg/l of total hardness
[2] Soft reconstituted water of 42 mg/l of total hardness

TABLE 3

Toxicity of N-(2-hydroxyethyl) Digeranylamine (50% Formulation) Exposed to Fish in 4,000 Liter Outdoor Plastic Pool

| Species | % kill for 96 hour exposure to toxicant (mg/l) | | | |
|---|---|---|---|---|
| | 0.10 | 0.15 | 0.20 | 0.30 |
| Rainbow trout (*Salmo gairdneri*) | 100 | 100 | 100 | 100 |
| Goldfish (*Carassius auratus*) | 0 | 0 | 0 | 0 |
| Carp (small) (*Cyprinus carpio*) | 100 | 100 | 100 | 100 |
| Carp (large) (*Cyprinus carpio*) | 27 | 66 | 100 | 100 |
| Grass carp (*Ctenopharyngodon idella*) | 0 | 0 | 0 | 0 |
| Fathead minnow (*Pimephales promelas*) | 0 | 10 | 10 | 80 |
| White sucker (*Catostomus commersoni*) | 20 | 70 | 100 | 100 |
| Largemouth buffalo (*Ictibous cyprinellus*) | 0 | 20 | 20 | 100 |
| Black bullhead (*Ictalurus melas*) | 0 | 0 | 0 | 0 |
| Channel catfish (*Ictalurus punctatus*) | 0 | 0 | 0 | 40 |
| Green sunfish (*Lepomis cyanellus*) | 0 | 0 | 0 | 0 |
| Bluegill (*Lepomis macrochirus*) | 0 | 0 | 0 | 0 |
| Largemouth bass (*Micropterus salmoides*) | 0 | 0 | 0 | 0 |
| Yellow perch (*Perca flavescens*) | 0 | 30 | 0 | 50 |
| Walleye (*Sitzostedion vitreum*) | 0 | 10 | 0 | 0 |

TABLE 4

Toxicity of N-(2-hydroxyethyl) Digeranylamino (tech) to green sunfish in soft water of different pH's at 12 C

| pH | LC50 and 95% confidence interval (mg/liter) at | | | |
|---|---|---|---|---|
| | 3 hours | 6 hours | 24 hours | 96 hours |
| 6.0 | 6.34 | 5.00 | 2.84 | 1.85 |
| | 5.57–7.21 | 4.36–5.73 | 2.30–3.52 | 1.57–2.19 |
| 7.5 | 2.47 | 1.64 | 1.00 | 0.829 |
| | 2.06–2.96 | 1.43–1.88 | 0.893–1.12 | 0.739–0.930 |
| 8.0 | — | — | 0.520 | 0.520 |
| | | | 0.464–0.582 | 0.464–0.582 |
| 9.0 | 0.870 | — | 0.360 | 0.268 |
| | 0.750–1.01 | | 0.298–0.435 | 0.210–0.341 |

What is claimed is:

1. A process for controlling fish populations which comprises treating the water wherein said fish reside with a piscicidally effective amount of an aminoalkanol toxicant or water-soluble salt thereof, having the formula:

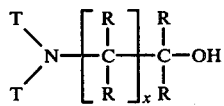

wherein:
T is a radical selected from the group consisting of geranyl, citronellyl, bupleuryl, neryl, lavandulyl, linalyl, myrcenyl, isobornyl and tetrahydrogeranyl;
R is independently hydrogen or lower alkyl radical containing one to four carbon atoms; and
X is an integer of 1 to 4.

2. The process according to claim 1 wherein said toxicant is applied at an effective rate of from about 0.03 to 10 parts active toxicant per million parts of water treated.

3. The process according to claim 1 wherein said water-soluble salt is selected from the group consisting of inorganic acid salts, organic acid salts, and quaternary ammonium salts of said amino-alkanol toxicant.

4. The process of claim 1 wherein the toxicant is applied to the water as a hydrochloride salt.

5. The process of claim 1 wherein the toxicant is N-(2-hydroxyethyl) digeranylamine.

6. The process of claim 5 wherein a 50% aqueous solution of N-(2-hydroxyethyl) digeranylamine hydrochloride is applied at an effective rate of from 0.03 to 10 parts active toxicant per million parts of water treated.

7. The process of claim 1 wherein T is 3,7-dimethyloctyl.

8. The process of claim 1 wherein the toxicant is N-(2-hydroxyethyl) di(3,7-dimethyloctyl) amine.

9. The process of claim 1 wherein T is isobornyl.

10. The process of claim 1 wherein the toxicant is the hydrochloride of N-(2-hydroxyethyl) diisobornylamine.

11. The process of claim 1 wherein the controlled species is common carp (*Cyprinus carpio*).

12. The process of claim 1 wherein the controlled species is white sucker (*Catostomus commersoni*).

13. The process of claim 1 where T is geranyl.

14. A process for selectively controlling undesirable species of fish, especially carp or white sucker species, in a water environment where other desirable species of fish are present, which comprises treating the water wherein said fish reside with a piscicidally effective amount of N-(2-hydroxyethyl) digeranylamine.

15. The process of claim 14 wherein the water is treated with 0.05 to 0.13 parts N-(2-hydroxyethyl) digeranylamine per million parts of water.

16. A process for selectively controlling undesirable species of fish, especially carp or white sucker species, in a water environment where other desirable species of fish are present which comprises treating the water wherein said fish reside with a piscicidally effective amount of an aminoalkanol toxicant having the formula:

wherein:
T is a radical selected from the group consisting of geranyl, citronellyl, bupleuryl, neryl, lavandulyl, linalyl, myrcenyl, isobornyl and tetrahydrogeranyl;
R is independently hydrogen or lower alkyl radical containing one to four carbon atoms; and
X is an integer of 1 to 4.

UNITED STATES PATENT AND TRADEMARK OFFICE
CERTIFICATE OF CORRECTION

PATENT NO. : 4,174,406
DATED : November 13, 1979
INVENTOR(S) : Carl Bordenca

It is certified that error appears in the above-identified patent and that said Letters Patent are hereby corrected as shown below:

Col. 1, line 21 bridging line 22, change "antimyein" to read --antimycin--; Col. 1, line 28, change "certai" to read --certain--; Col. 3, line 41, following the word "salt" insert --;--; Col. 4, line 55, change "N-(5-hydroxypentyl)digeranylamino" to read --N-(5-hydroxypentyl)digeranylamine--; Col. 8, line 60 after the term "pH." delete --antimycin--; Col. 9, Table 1 the entry under Lake trout appearing in the third column "0.0380-0.0680" should be transposed to the fourth column (96 hours) to appear directly under "0.0570".

Signed and Sealed this

Twenty-sixth Day of February 1980

[SEAL]

Attest:

SIDNEY A. DIAMOND

Attesting Officer

Commissioner of Patents and Trademarks